(12) United States Patent
Weinberg

(10) Patent No.: US 6,355,682 B1
(45) Date of Patent: Mar. 12, 2002

(54) TREATMENT OF ACUTE RENAL FAILURE BY ADMINISTRATION OF N-ACETYLCYSTEINE

(75) Inventor: Assa Weinberg, 344 N. Fairfax Ave., Los Angeles, CA (US) 90036

(73) Assignee: Assa Weinberg, Los Angeles, CA (US)

( * ) Notice: Subject to any disclaimer, the term of this patent is extended or adjusted under 35 U.S.C. 154(b) by 0 days.

(21) Appl. No.: 09/854,342

(22) Filed: May 11, 2001

(51) Int. Cl.⁷ .............................................. A61K 31/195
(52) U.S. Cl. ...................................................... 514/562
(58) Field of Search ........................................ 514/562

(56) References Cited

U.S. PATENT DOCUMENTS 5,607,974 A * 3/1997 Droge et al. ................. 514/562
5,766,873 A * 6/1998 Noble et al. .................... 435/25

* cited by examiner

*Primary Examiner*—Raymond Henley, III
(74) *Attorney, Agent, or Firm*—Squire, Sanders & Dempsey LLP.; Dave B. Koo

(57) ABSTRACT

A method for treating the damages caused by an acute renal failure is disclosed. The method according to the present invention comprises the administration of a therapeutically effective dose of N-acetylcysteine.

11 Claims, No Drawings

TREATMENT OF ACUTE RENAL FAILURE BY ADMINISTRATION OF N-ACETYLCYSTEINE

FIELD OF THE INVENTION

The present invention relates to the field of treatment of patients who have been afflicted with acute renal failure.

BACKGROUND OF THE INVENTION

Acute renal failure or a rapid deterioration of the renal function is a common disturbance during which the kidneys' filtering capacity is lost and, as a result, a rapid accumulation of waste material, mainly nitrogenous products, occurs in the body. One of the most common causes for such renal failure is due to the reduction or interruption of the blood supply to the kidneys. Such reduction or interruption of the blood supply to the kidneys could be generally described as renal ischemia.

There are multiple medical conditions that could cause the interruption of the renal circulation. Depending on the duration of an interruption, the outcome of an acute renal failure can be quite devastating. Every cardiovascular event associated with hypotension has a potential of causing a reduction in renal vascular supply. Other conditions, such as gastrointestinal hemorrage, extensive burn, trauma, surgery or anesthesia may also cause hypovolemia, i.e. a low blood volume. Hypovolemia may lead to a dramatic reduction in the blood circulating to the kidneys which may lead to a rapid deterioration in renal function.

The outcome of an acute renal failure is quite grim, especially for patients with trauma as well as patients of advanced age with serious underlying illnesses. Many patients, even after the initial recovery from an acute renal failure, remain with a substantial loss of the filtering capacity of the kidneys, and often thereafter require hemodialysis. Presently, the treatment of acute renal failures is limited to the management of the fluid and the electrolyte complications. Patients affected by an acute renal failure are thus left with no meaningful treatments to restore the function of the damaged renal tissues.

SUMMARY OF THE INVENTION

The invention described herein is a novel method of treating and reversing the damages associated with acute renal failures. The method according to the present invention comprises the administration of a therapeutically effective dose of N-acetycysteine, a drug having a previously unknown property to reverse damages caused by acute renal failures.

DESCRIPTION OF THE INVENTION

N-acetylcysteis the N-acetyl derivative of L-cystein. The empirical formula of N-acetylcysteinen is $C_5H_9NO_5S$ and its molecular weight is 163.191. Its structural formula is:

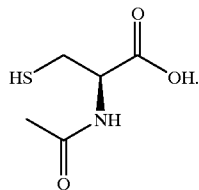

N-acetycysteine is known to have a potent antioxidant activity and has been primarily used in the treatment of acetylaminophen (Tylenol) overdose toxicity. Its mucolytic property has been frequently used in the treatment of bronchitis and other respiratory conditions.

Use of N-acetycysteine in the treatment of damages caused by acute renal failures has been previously unknown. According to the present invention, administering a therapeutically effective amount of N-acetycysteine to patients can treat and reverse the renal and associated functional damages that are caused by the interruption of the blood supply to the kidney tissues.

The effective amount of N-acetycysteine according to the present invention is not limited to the dosages described in the clinical case reports herein, but may range from the daily dosage of 10 mg to 150 mg per kg of body weight, and 200 mg to 2400 mg per day depending on other factors such as the severity of the damage and the general physical conditions of a particular patient. The preferred dosage is about 20 mg per kg body weight, and about 600 mg to 1200 mg per day. The drug may be a solution of N-acetycysteine, which currently exists in ten and twenty percent solutions. Additionally, the drug may be prepared and administered in other forms including, without limitation, as a tablet, power, capsule, and injection.

The useful therapeutic property of N-acetycysteine for treating patients affected by acute renal failures is demonstrated by the following clinical case reports.

Case No. 1

An 85 years old lady was admitted to the intensive care unit in a cardiogenic shock. Following an intense anti-platelet and anti-coagulant treatment, her hemodynamic status improved, but a reduction in her urine output was noticed. On the following day, the diagnosis of an acute renal failure was established by the standard criteria and the patient's urine output continued to decrease while her Blood Urea Nitrogen (BUN) and Creatinin rose rapidly. She became nearly completely anuric, and a nephrologist ordered the insertion of a dialysis catheter in preparation for rescue hemodialysis. 600 mg of N-acetycysteine in a 20% solution was administered to the patient every twelve hours. The next day, the rise of BUN and Creatinin stopped, and the insertion of the dialysis catheter was delayed. Over the next several days, N-acetycysteine was administered at a dose of 10 mg/kg twice daily and the renal function returned to normal. Dialysis was no longer required.

Case No. 2

A 40 years old businessman was admitted to the intensive care unit with a hypovolemic shock because of an acute pancreatitis. Over the next several days, his hemodynamic condition stabilized, but a rapid deterioration in renal function was discovered. His BUN and Creatinin values increased from normal to five times the normal level. Because of the impact of the fluids accumulation on his cardiovascular state and the development of fluids overload and congestive heart failure, a nephrologist consultant ordered the insertion of a Quinton catheter to institute hemodialysis. At the same time, N-acetycysteine in a 20% solution in the dose of 20 mg/kg was administered every twelve hours. The rise in his BUN and Creatinin stopped, and his renal function returned to normal over the next seventy-two hours. Dialysis was no longer required.

Case No. 3

An 87 years old woman was admitted to the intensive care unit with a multi-organ failure syndrome. Several hours prior to her admission, she developed a ventricular arrythmia which led to a cardiac arrest. She required multiple cardioversion electrical shocks for the establishment of a normal cardiac rhythm. She required a tracheal intubation and mechanical ventilation, as well as multiple infusions of pressure support medication. On the following day, she was found to be in an acute renal failure with rapidly progressive BUN and Creatinin values, and a urine output of less than 100 cc per day. In this particular case, the duration of the hypotensive episode was estimated to be several hours. According to the nephrology consultant, the chances of recovering her renal function were extremely low. She was given N-acetycysteine via nasogastric tube at a dose of 20 mg/kg every twelve hours. Over the next several days, her BUN and Creatinin progressively declined. Her urine output increased to the normal level indicating the normalization of her kidney functions.

Case No. 4

An 85 years old diabetic patient was admitted to a community hospital because of a persistent urosepsis. She was known to have multiple chronic disorders including high blood pressure, congestive heart failure, morbid obesity, diabetic nephropathy, and chronic skin ulcers. Several days prior to the admission, she developed an infectious cellulitis of the lower extremities. Upon admission, cultures were taken from her skin ulcers and urine. Her skin ulcers grew methicillin resistant, Staphilococus Aurous, and her urine grew a multi-drug resistant gram negative bacilli which were sensitive only to Imipenim. She was placed on a combination of IV Vancomycin and Imipenim. Her clinical condition improved. In spite of a careful monitoring to the antibiotic dosage, she developed an acute renal failure several days after the institution of the antibiotic therapy. The two antibiotics administered are well known for their nephrotoxicity. Her BUN and Creatinin rapidly rose to five times the normal level. Her Creatinin clearance declined to 11 ml/minute (normal for her age is above 65 ml/min.). The family was notified about the need for dialysis. The patient was placed on 10 mg/kg N-acetycysteine every twelve hours. The Bun/Creatinin progressively declined, and the urine output, which was dramatically reduced the previous days, returned to normal within several days. Two weeks after the onset of the renal toxicity, her Creatinin clearance increased to 22 ml/min. and dialysis was no longer required.

Case No. 5

A 52 years old woman with a severe chronic renal failure secondary to pauci-immune glomerulo nephritis was admitted to a tertiary hospital because of the deterioration of her chronic renal failure. She was known to have Sjogren syndrome for many years associated with a severe interstitial pulmonary fibrosis. One week prior to the admission, she developed a severe upper respiratory infection which required the use of antibiotic—Ciprofloxacin. After one week on the antibiotic, she noticed a severe decline in her urine output and general malaise. The blood tests taken before her admission revealed that her serum potassium rose to 6.8. As the renal function prior to the infectious event was very poor, it was thought to be the final event before the patient would need permanent intermittent hemodialysis. Upon admission, she was given N-acetylcysteine 20 mg/kg every twelve hours. Within 24 hours, her urine volume substantially increased and her potassium level normalized. She remained on N-acetycysteine at 600 mg twice daily. She no longer required any hemodialysis.

The above cases indicate the therapeutic efficacy of N-acetycysteine in restoration of the renal function in patients affected by an acute renal failure from hypotension or ichemic episodes. N-acetycysteine is capable of affecting the clinical and functional outcome of patients with an acute renal failure, and reducing and eliminating the need for hemodialysis.

While the foregoing description defines an embodiment of the present invention, it is to be understood that it is subject to many modifications and changes without departing from the spirit and scope of the appended claims.

What is claimed is:

1. A method for treating patients with an acute renal failure comprising:
   administering a therapeutically effective amount of N-acetylcysteine.

2. The method according to claim 1, wherein said therapeutically effective amount of N-acetylcysteine is the effective amount necessary to treat and reverse damages of renal tissues caused by acute renal failure.

3. The method according to claim 1, wherein said acute renal failure is caused by a reduction of the renal blood circulation, wherein said reduction is due to conditions comprising renal ischemia, hypotension, hypovolemia, gastrointestinal hemorrage, burns, trauma, anesthesia, and antibiotic toxicity.

4. The method according to claim 1, wherein said therapeutically effective amount of N-acetycysteine is a dosage between 200 mg to 2400 mg per day.

5. The method according to claim 1, wherein said therapeutically effective amount of N-acetylcysteine is a dosage between 600 mg to 1200 mg per day.

6. The method according to claim 1, wherein said therapeutically effective amount of N-acetylcysteine is a daily dosage of 10 mg to 150 mg per kg of body weight.

7. The method according to claim 1, wherein said therapeutically effective amount of N-acetylcysteine is a daily dosage of about 20 mg per kg of body weight.

8. The method according to claim 1, wherein said N-acetylcysteine is in a twenty percent solution.

9. The method according to claim 1, wherein said N-acetylcysteine is in a ten percent solution.

10. The method according to claim 1, wherein said N-acetylcysteine is in a form selected from the group consisting of tablets, capsules, power, solutions, and injections.

11. A method for diagnosing and treating acute renal failure comprising:
    taking a blood sample and measuring the BUN;
    determining if the BUN is above a normal range;
    administering a therapeutically effective amount of N-acetylcysteine; and
    taking a subsequent blood sample and testing for BUN to determine if BUN has increased since last measurement.

* * * * *